(12) United States Patent
Park et al.

(10) Patent No.: US 10,123,778 B2
(45) Date of Patent: Nov. 13, 2018

(54) DIAGNOSIS AIDING APPARATUS AND METHOD TO PROVIDE DIAGNOSIS INFORMATION AND DIAGNOSIS SYSTEM THEREOF

(71) Applicant: Samsung Electronics Co., Ltd., Suwon-si (KR)

(72) Inventors: Moon-Ho Park, Hwaseong-si (KR); Yeong-Kyeong Seong, Yongin-si (KR); Jong-Ha Lee, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 73 days.

(21) Appl. No.: 14/176,657

(22) Filed: Feb. 10, 2014

(65) Prior Publication Data

US 2014/0228687 A1   Aug. 14, 2014

(30) Foreign Application Priority Data

Feb. 8, 2013 (KR) ........................ 10-2013-0014600

(51) Int. Cl.
 *A61B 8/00* (2006.01)
 *A61B 8/08* (2006.01)
 *A61B 8/14* (2006.01)

(52) U.S. Cl.
 CPC .............. *A61B 8/465* (2013.01); *A61B 8/085* (2013.01); *A61B 8/0858* (2013.01); *A61B 8/14* (2013.01); *A61B 8/463* (2013.01); *A61B 8/466* (2013.01); *A61B 8/483* (2013.01); *A61B 8/5223* (2013.01);

(Continued)

(58) Field of Classification Search
 CPC ....... A61B 8/465; A61B 8/085; A61B 8/0858; A61B 8/14; A61B 8/463; A61B 8/466; A61B 8/468; A61B 8/483; A61B 8/5223
 See application file for complete search history.

(56) References Cited

U.S. PATENT DOCUMENTS 6,480,732 B1 * 11/2002 Tanaka ................ A61B 8/5238
 128/922
7,633,501 B2   12/2009 Wood et al.
(Continued)

FOREIGN PATENT DOCUMENTS

CN    101259026 A    9/2008
JP    2011-167331 A    9/2011
(Continued)

OTHER PUBLICATIONS

Haung, S., Chen, Y. Moon, W., "Neural Network Analysis Applied to Tumor Segmentation on 3D Breast Ultrasound Images", ISBI, 2008, pp. 1303-1306.*

(Continued)

*Primary Examiner* — Rochelle Turchen
*Assistant Examiner* — Joanne Hoffman
(74) *Attorney, Agent, or Firm* — Jefferson IP Law, LLP (57) ABSTRACT

A diagnosis aiding apparatus and method to provide diagnosis information is provided. The diagnosis aiding apparatus includes an information display unit configured to display a reference cross-section of an image, display diagnosis information belonging to the reference cross-section, and display diagnosis information corresponding to a different cross-section within the reference cross-section displayed.

38 Claims, 7 Drawing Sheets

(52) U.S. Cl.
CPC ............... *A61B 8/54* (2013.01); *A61B 8/468* (2013.01); *A61B 8/5246* (2013.01)

(56) References Cited

U.S. PATENT DOCUMENTS

| | | | |
|---|---|---|---|
| 7,930,014 B2* | 4/2011 | Huennekens | A61B 6/504 382/159 |
| 2003/0095697 A1 | 5/2003 | Wood et al. | |
| 2007/0003124 A1* | 1/2007 | Wood | A61B 6/032 382/131 |
| 2007/0255139 A1 | 11/2007 | Deschinger et al. | |
| 2008/0008369 A1* | 1/2008 | Koptenko | G06K 9/4604 382/128 |
| 2008/0221446 A1* | 9/2008 | Washburn | A61B 8/00 600/437 |
| 2009/0136109 A1* | 5/2009 | Salgo | A61B 8/0858 382/131 |
| 2010/0040200 A1 | 2/2010 | Ema et al. | |
| 2011/0109650 A1* | 5/2011 | Kreeger | G06F 19/3406 345/634 |
| 2012/0253173 A1* | 10/2012 | Endo | G06T 11/008 600/411 |
| 2013/0169632 A1 | 7/2013 | Sawayama | |

FOREIGN PATENT DOCUMENTS

| | | |
|---|---|---|
| KR | 10-2008-0069307 A | 7/2008 |
| KR | 10-2010-0071595 A | 6/2010 |
| WO | WO 2012/043200 A1 | 4/2012 |

OTHER PUBLICATIONS

Extended European Search Report dated May 27, 2014 in counterpart European Application EP 14154511.1 (7 pages).

* cited by examiner

DIAGNOSIS AIDING APPARATUS AND METHOD TO PROVIDE DIAGNOSIS INFORMATION AND DIAGNOSIS SYSTEM THEREOF

CROSS-REFERENCE TO RELATED APPLICATION

This application claims the benefit under 35 U.S.C. § 119(a) of Korean Patent Application No. 10-2013-0014600, filed on Feb. 8, 2013, the entire disclosure of which is incorporated herein by reference for all purposes.

BACKGROUND

1. Field

The following description relates to diagnosis aiding apparatus and method to provide diagnosis information and a diagnosis system thereof.

2. Description of the Related Art

In medical industry, three-dimensional (3D) images are obtained using a 3D ultrasound probe to analyze lesions. For instance, the 3D ultrasound probe is used to check whether a lesion exists from 3D volume data in each cross-section of a 3D image. However, a medical practitioner, technician or user has difficulty in extracting each piece of significant information from various cross-sections of the 3D volume data. In addition, a Multi-Planar Reformatting/Reconstruction (MPR) technique, which is utilized to analyze lesions existing in the 3D volume data in an ultrasound diagnosis system, does not allow to check various cross-sections at the same time. As a result, a lesion diagnosis is generally performed using one cross-section.

SUMMARY

In accordance with an illustrative configuration, there is provided a diagnosis aiding apparatus, including an information display configured to display a reference cross-section of an image, display diagnosis information corresponding to the reference cross-section, and display diagnosis information corresponding to a different cross-section within the reference cross-section displayed.

The diagnosis information corresponding to each cross-section includes at least one of a lesion, shape, texture, and boundary of the lesion, a result of a diagnosis of the lesion, distance information relative to the reference cross-section and bookmark information.

In response to diagnosis information corresponding to one or more different cross-sections other than the reference cross-section, the information display unit displays the diagnosis information corresponding to each of the one or more different cross-sections differently based on distance information between the reference cross-section and each of the one or more different cross-sections.

The information display unit displays the diagnosis information differently based on the distance information, at least one of a type of color, darkness of a color, a type of line and darkness of a line for the diagnosis information of each of the one or more different cross-sections from that of the diagnosis information of the reference cross-section.

In response to diagnosis information located on each of a front side and a rear side of the reference cross-section, the information display unit displays the diagnosis information located on each of the front side and the rear side differently based on at least one of a type of color, darkness of a color, a type of line and darkness of a line for the diagnosis information located on one of the front side and the rear side from that of the diagnosis information located on the other side.

The diagnosis aiding apparatus includes an input processing unit configured to perform an operation in accordance with diagnosis information selected by a user from among a collection of diagnosis information displayed within the reference cross-section.

In response to diagnosis information corresponding to a different cross-section from the reference cross-section, being selected, the input processing unit controls the different cross-section.

The input processing unit controls the different cross-section to be displayed for a length of time, and controls the reference cross-section to be displayed on a screen again after the length of time.

In response to the different cross-section, the information display unit displays, within the different cross-section displayed on a screen, both the diagnosis information corresponding to the different cross-section and diagnosis information corresponding to a cross-section that disappears on the screen due to the displaying of the different cross-section.

The input processing unit controls the information display unit to display detailed information of the diagnosis information at a predetermined location within the reference cross-section in an overlapping manner.

The input processing unit generates a bookmark on the displayed reference cross-section, and stores bookmark information containing a location of the bookmark and additional memo information input by the user.

In accordance with an illustrative example, there is provided a diagnosis aiding method, including displaying a reference cross-section of an image o on a screen; displaying diagnosis information corresponding to the reference cross-section within the reference cross-section; and displaying diagnosis information corresponding to a different cross-section within the reference cross-section.

The diagnosis information corresponding to each cross-section includes at least one of a lesion, shape, texture, and boundary of the lesion, a result of a diagnosis of the lesion, distance information relative to the reference cross-section and bookmark information.

The diagnosis aiding method also includes configuring the displaying of the diagnosis information to correspond to the different cross-section includes displaying the diagnosis information corresponding to the different cross-section differently based on the distance information relative to the reference cross-section.

The displaying of the diagnosis information corresponding to the different cross-section includes displaying the diagnosis information corresponding to the different cross-section differently based on at least one of a type of color, darkness of a color, a type of line and darkness of a line for the diagnosis information corresponding to the different cross-section from that of the diagnosis information corresponding to the reference cross-section.

The displaying of the diagnosis information corresponding to the different cross-section includes, in response to diagnosis information located on each of a front side and a rear side of the reference cross-section, displaying the diagnosis information located on one of the front side and the rear side differently based on at least one of a type of color, darkness of a color, a type of line and darkness of a line between the diagnosis information located on one of the front side and the rear side from that of the diagnosis information located on the other side.

The diagnosis aiding method also includes in response to diagnosis information selected by a user from a collection of diagnosis information displayed within the reference cross-section on the screen, performing an operation in accordance with the user's selection.

In response to the selected diagnosis information corresponding to the different cross-section, the performing of the predetermined operation includes controlling the different cross-section to be displayed on the screen.

The performing of the operation includes controlling the different cross-section on the screen for a length of time and controlling the reference cross-section to be displayed on the screen again after the length of time.

The performing of the operation includes controlling detailed information of the selected diagnosis information to be displayed on a predetermined location within the reference cross-section in an overlapping manner.

The diagnosis aiding method also includes generating a bookmark within the reference cross-section on the screen; and storing bookmark information containing a location of the bookmark and additional memo information of the bookmark.

In accordance with another illustrative example, there is provided a diagnosis system, including an diagnosis apparatus configured to detect a lesion from a reference cross-section of an image, analyze the lesion and generate diagnosis information corresponding to the reference-cross section regarding the lesion; and a diagnosis aiding apparatus configured to display the reference cross-section on a screen and display, within the reference cross-section, the diagnosis information corresponding to the reference cross-section and diagnosis information corresponding to a different cross-section other than the reference cross-section.

The diagnosis information corresponding to each cross-section includes at least one of distance information between the reference cross-section and a previously obtained cross-section, shape, texture, and boundary of the lesion and a result of a diagnosis of the lesion.

The diagnosis aiding apparatus displays the diagnosis information corresponding to the reference cross-section and the diagnosis information corresponding to the different cross-section differently based on distance information between the reference cross-section and the different cross-section.

In response to the diagnosis information of the different cross-section, selected by a user, the diagnosis aiding apparatus displays the different cross-section on the screen.

When displaying the different cross-section containing the selected diagnosis information on the screen, the diagnosis aiding apparatus displays, within the different cross-section, diagnosis information corresponding to the different cross-section and diagnosis information of a cross-section, which disappears on the screen due to the displaying of the different cross-section.

In accordance with another illustrative example, there is provided a diagnosis aiding apparatus including an information display unit configured to display, within a reference cross-section of an image, diagnosis information corresponding to the reference cross-section and diagnosis information corresponding to a different cross-section, and display distance information between the reference cross-section and the different cross-section as diagnosis information of an area of interest in the image.

The diagnosis information includes lesion diagnosis information and bookmark information.

The information display unit displays the diagnosis information of the reference cross-section and the diagnosis information of the different cross-section based on distance information between the reference cross-section and the different cross-section.

The information display unit displays the diagnosis information of the reference cross-section and the diagnosis information of the different cross-section differently based on the distance information, a type of line, type of colors, darkness of a color, or darkness of a line.

The information display unit displays the different cross-section for a length of time, and displays the reference cross-section again after the length of time.

32. The diagnosis aiding apparatus as recited in claim 27, wherein the lesion diagnosis information includes at least one of shape, texture, and boundary of a lesion, and a result of a diagnosis of the lesion.

The information display unit displays bookmark information input from a user as a suspected area or an area required to be further diagnosed.

The information display unit displays within the reference cross-section the diagnosis information of the different cross-section and the diagnosis information located on a front side and a rear side or on a left side and a front side of the reference cross-section.

The diagnosis information includes lesion analytical information and bookmark information.

The lesion analytical information includes shape, texture, and boundary of the lesion, and a result of the diagnosis of the lesion.

When displaying a lesion or a bookmark corresponding to the different cross-section as the diagnosis information within the reference cross-section, the information display unit displays distance information between the reference cross-section and the different cross-section as diagnosis information.

The diagnosis aiding apparatus also includes an input processing unit configured to generate a bookmark at a location in the reference cross-section and configured to receive memo information about the bookmark.

In accordance with another illustrative example, there is provided an apparatus, including an image displaying unit configured to display a reference cross-section of an image; and an information display unit configured to display a lesion at a location in the reference cross-section and lesions corresponding to different cross-sections at other locations in the reference cross-section providing a relative location of each lesion in relation to the reference cross-section.

The information display unit displays detailed information regarding the lesions or the bookmarks at a location on a screen.

The information display unit displays all lesions or diagnosis information corresponding to different cross-sections, or some of all the lesions or diagnosis information corresponding to different cross-sections are displayed within the reference cross-section.

The apparatus also includes an image obtaining unit configured to generate three-dimensional (3D) volume image data using cross-sections of an area of interest in a patient; and a lesion analyzing unit configured to calculate distance information between the cross-sections to generate diagnosis information of the area of interest.

The apparatus also includes an input processing unit configured to generate a bookmark at a location in the reference cross-section and configured to receive memo information about the bookmark.

Other features and aspects will be apparent from the following detailed description, the drawings, and the claims.

BRIEF DESCRIPTION OF THE DRAWINGS

The accompanying drawings, which are included to provide a further understanding of the invention and are incorporated in and constitute a part of this specification, illustrate embodiments of the invention, and together with the description serve to explain the principles of the invention.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following description is provided to assist the reader in gaining a comprehensive understanding of the methods, apparatuses, and/or systems described herein. Accordingly, various changes, modifications, and equivalents of the methods, apparatuses, and/or systems described herein will suggest themselves to those of ordinary skill in the art. Also, descriptions of well-known functions and constructions may be omitted for increased clarity and conciseness.

The terminology used herein is for the purpose of describing particular embodiments only and is not intended to be limiting of the present invention. As used herein, the singular forms "a," "an" and "the" are intended to include the plural forms as well, unless the context clearly indicates otherwise.

Unless otherwise defined, all terms (including technical and scientific terms) used herein have the same meaning as commonly understood by one of ordinary skill in the art to which the present invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figure 1:
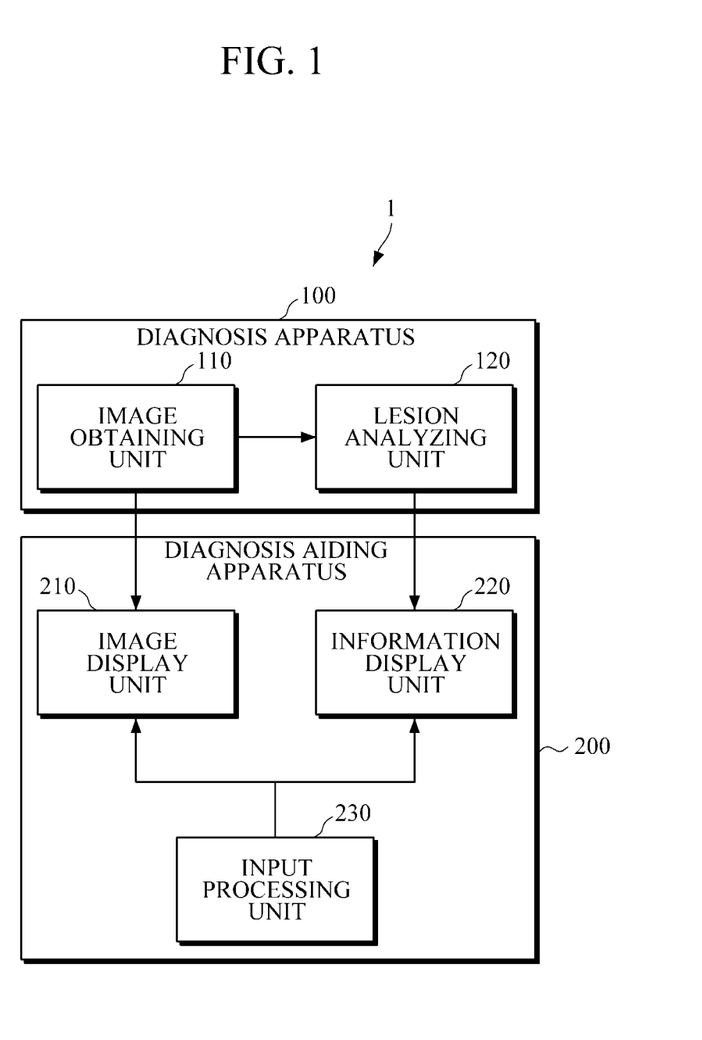
FIG. 1 is a block diagram illustrating a diagnosis system, according to an illustrative example.

FIG. 1 is a diagram illustrating a diagnosis system, according to an illustrative example. Referring to FIG. 1, the diagnosis system 1 includes a diagnosis apparatus 100 and a diagnosis aiding apparatus 200.

In response to a reference cross-section of an image obtained from an ultrasound measuring device, the diagnosis apparatus 100 detects a lesion from a reference cross-section and generates diagnosis information of the detected lesion. As illustrated in FIG. 1, the diagnosis apparatus 100 includes an image obtaining unit 110 and a lesion analyzing unit 120.

The image obtaining unit 110 obtains an ultrasound image using an ultrasound measuring device (for example, a ultrasound probe). A user moves the ultrasound measuring device to measure cross-sections of a lesion, an organ of, or an area of interest in a patient or a subject. In one example the patient or the subject may be a person or animal. In turn, the image obtaining unit 110 generates three-dimensional (3D) volume image data using image data from each cross-section of the organ or area of interest. The image obtaining unit 110 receives an image measured from the ultrasound measuring device.

The lesion analyzing unit 120 detects and analyzes a lesion existing in the 3D volume image data using various lesion detection algorithms or techniques. In one example, the lesion detection technique is not limited to be a specific algorithm, but may include every well-known lesion detection algorithm. Each detected lesion may be stored, for instance, based on the cross-sections that forms a 3D volume image. The diagnosis device 100 may further include a diagnosis information database (DB) (not illustrated) or a diagnosis information storage (not illustrated) in which the lesion analyzing unit 120 stores the detected lesion as diagnosis information with corresponding identification information of the cross-section that includes the detected lesion.

The lesion analyzing unit 120 analyses the detected lesion and generates diagnosis information about the detected lesion. The diagnosis information may include a lesion, shape, texture, and boundary of the lesion, and whether the lesion is benign or malignant. In addition, the lesion analyzing unit 120 further calculates distance information between cross-sections obtained by the image obtaining unit 110, and generates the distance information as diagnosis information. The lesion analyzing unit 120 stores the generated diagnosis information in the diagnosis information DB (not illustrated).

The diagnosis aiding unit 200 aids the lesion diagnosis in various ways using the diagnosis information generated in the diagnosis apparatus 100 to make it easy to diagnose a lesion. The diagnosis aiding apparatus 200 displays on a screen a reference cross-section of the image obtained from the diagnosis apparatus 100, the diagnosis information of the reference cross-section, and diagnosis information of a different cross-section excluding the reference cross-section. As a result, the diagnosis aiding unit 200 is configured to prevent an omission of diagnosing a lesion based on 3D volume data of a cross-section that forms a 3D volume image cross-section.

In accord with an illustrative example, the diagnosis aiding apparatus 200 includes an image display unit 210, an information display unit 220 and an input processing unit 230.

The image display unit 210 displays on a screen a reference cross-section of the image obtained from the diagnosis apparatus 100 or from an ultrasound measuring device. The image display unit 210 displays the reference cross-section and a generated 3D volume image using, in one example, Multi-Planner Reformatting/Reconstruction (MPR). A person of ordinary skill in the relevant art will appreciate that other reformatting and/or reconstructions processes to MPR may be used to display the reference cross-section and a generated 3D volume image. Alternatively, the image display unit 210 displays the reference cross-section in full view on the screen.

When diagnosis information is shown in the reference cross-section of the image obtained from the diagnosis apparatus 100, the information display unit 220 displays the diagnosis information within the reference cross-section on the screen. In one example, the information display unit 220 displays, within the displayed reference cross-section, diagnosis information of a different cross-section excluding the reference cross-section and diagnosis information located on a front side and a rear side of the reference cross-section. In an alternative example, the information display unit 220 displays, within the displayed reference cross-section, diagnosis information of a different cross-section excluding the reference cross-section and diagnosis information located on a left side and a right side of the reference cross-section.

Diagnosis information may include lesion analytical information and bookmark information. The lesion analytical information includes a lesion analyzed by the lesion analyzing unit 120, shape, texture, and boundary of the lesion, and a result of the diagnosis of the lesion. User inputs generate the bookmark information. A bookmark is a particular point or area of the reference cross-section that a user enters and desires to be further analyzed or explored. The bookmark information is information that the user may enter corresponding to a bookmark. When displaying a lesion or a bookmark corresponding to a different cross-section as diagnosis information within the reference cross-section, the information display unit 220 displays distance information between the reference cross-section and the different cross-section, and displays the calculated distance information as diagnosis information.

As described with reference to FIGS. 2A to 2B, the information display unit 220 displays diagnosis information of the different cross-section within the reference cross-section in various ways, thereby helping a user to effectively detect lesions using ultrasound images without omitting relevant information to diagnose a lesion.

An input processing unit 230 receives various user inputs and performs an operation corresponding to each of the user inputs. For example, in response to a user selecting diagnosis information from among a collection of diagnosis information displayed within the reference cross-section of the image obtained from the diagnosis apparatus 100, the input processing unit 230 controls detailed information of the selected diagnosis information to be displayed within the reference cross-section or controls a cross-section containing the selected diagnosis information to be displayed on the screen. In the latter case, in one example, the input processing unit 230 controls the cross-section containing the selected diagnosis information to be displayed for a predetermined length of time and controls the reference cross-section to be displayed on the screen after the predetermined length of time. In one illustrative example, the predetermined length of time is configured to be a time between 1 second to 10 seconds. The predetermined length of time may be a time outside this illustrative range. In this way, the input processing unit 230 enables a user to move into a specific cross-section of the image to analyze a lesion therein, without physically moving the ultrasound measuring device (for example, a probe).

In addition, when a user requests to generate a bookmark within the reference cross-section, the input processing unit 230 generates the bookmark at a predetermined location within the reference cross-section and stores the location of the bookmark as bookmark information. In addition, when the user inputs additional memo information regarding the bookmark, the input processing unit 230 receives the memo information and stores the memo information as bookmark information. The bookmark information may be stored in a diagnosis information database or storage (not illustrated).

Under the control from the input processing unit 230, the image display unit 210 displays the different cross-section excluding the reference cross-section and containing the selected diagnosis information. In one example, when the input processing unit 230 displays the different cross-section containing the selected diagnosis information for a predetermined length of time, the image display unit 210 displays the cross-section on a screen, checks whether the predetermined length of time has lapsed, and displays the reference cross-section on the screen again after the predetermined length of time.

Under the control from the input processing unit 230, the information display unit 220 displays the detailed information of the selected diagnosis information on the reference cross-section. Alternatively, when the different cross-section containing the selected diagnosis information is displayed on the screen by the image display unit 210, the information display unit 220 displays, within the different cross-section, the diagnosis information associated with a cross-section that disappears on the screen due to the displaying of the different cross-section. For example, the information display unit 220 displays the diagnosis information located on a front side, a rear side, a left side or a right side of the different cross-section that is being displayed on the screen.

Although the image obtaining unit 110 and the lesion analyzing unit 120 are illustrated as part of the diagnosis apparatus 100, it can be appreciated that the image obtaining unit 110 and the lesion analyzing unit 120 may be integrally part of the diagnosis aiding apparatus 200.

The units and apparatuses described herein may be implemented using hardware components. The hardware components may include, for example, controllers, processors, generators, drivers, and other equivalent electronic components. The hardware components may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The hardware components may run an operating system (OS) and one or more software applications that run on the OS. The hardware components also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a hardware component may include multiple processors or a processor and a controller. In addition, different processing configurations are possible, such a parallel processors.

Figure 2A:
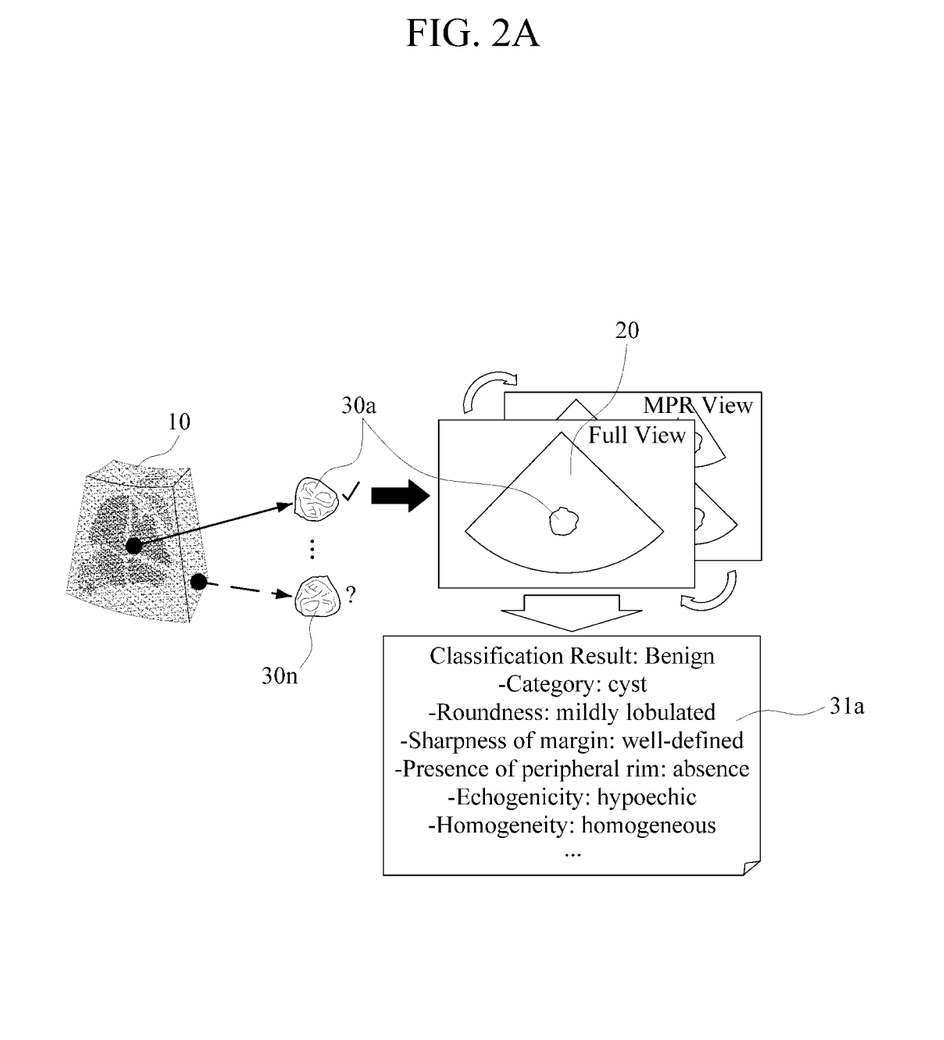
FIGS. 2A and 2B are diagrams illustrating an example in which diagnosis information is displayed.
Figure 2B:
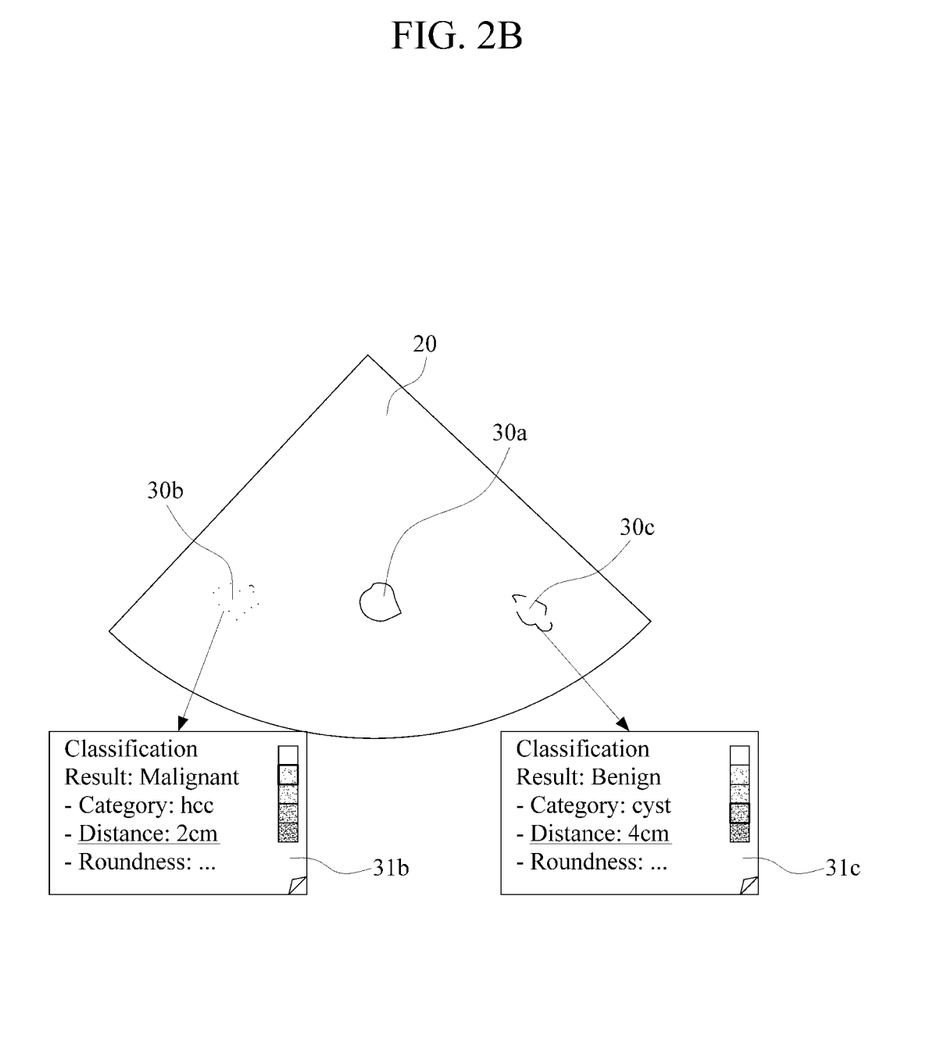

FIGS. 2A and 2B are diagrams illustrating an example of displaying lesion information in the reference cross-section.

Referring to FIG. 2A, the image obtaining unit 110 of the diagnosis apparatus 100 obtains cross-sections using signals from the ultrasound measuring device to output the three-dimensional (3D) volume image data to generate a 3D volume image 10. The lesion analyzing unit 120 detects and analyzes lesions 30*a* to 30*n* which respectively correspond to cross-sections of the 3D volume image 10. The image displaying unit 210 of the diagnosis aiding apparatus 200 displays the reference cross-section in a MRP view or in full view on a screen. The information display unit 220 displays a lesion 30*a* corresponding to a reference cross-section 20 at a requested location in the reference cross-section 20. In one example, the information display unit 220 displays diagnosis information 31*a* about the lesion 30*a* at a predetermined location on the screen. Alternatively, in response to the input processing unit 230 controlling detailed information of the selected lesion 30*a* to be displayed in response to a user selecting the lesion 30*a* displayed within the reference cross-section 20, the information display unit 220 displays the diagnosis information 31a at a requested location on the screen.

In another embodiment, referring to FIG. 2B, the information display unit 220 is able to display not only a lesion 30a corresponding to the reference cross-section 20 but also other lesions 30b and 30c corresponding to different cross-sections at other predetermined locations in the reference cross-section 20 on a screen. In addition, if any one of the different cross-sections contains bookmark information, the information display unit 220 may display the bookmark information at the predetermined locations in the reference cross-section 20.

The information display unit 220 may display the lesions 30b and 30c corresponding to the different cross-sections to be distinguishable from the lesion 30a corresponding to the reference cross-section 20 in various ways. For example, the information display unit 220 may display lesions or bookmarks between the reference cross-section and each of the different cross-sections in a distinguishable way by differentiating a type of color or darkness of a color between the lesions or bookmarks. Alternatively, the information display unit 220 may display lesions or bookmarks between the reference cross-section and each of the different cross-sections in a distinguishable way by differentiating a type of line or darkness of a line between the lesions or bookmarks. At this time, the information display unit 220 may display diagnosis information of a lesion or a bookmark corresponding to the different cross-section to be distinguishable from that of a lesion or a bookmark corresponding to the reference cross-section, based on distance information between the reference cross-section and the different cross-section. In this way, a user may be provided with a relative location of the different cross-section in relation to the reference cross-section 20. For example, the farther the diagnosis information is from the reference cross-section 20, a more blurred line or a lesser dark line may be used. In addition to the above, different type of lines or type of colors may be used between the reference cross-section and the different cross-section.

In addition, as illustrated in FIG. 2B, if there is diagnosis information 30b and 30c located on the front side and the rear side or the left side and the right side of the reference cross-section 20, the information display unit 220 displays the diagnosis information 30b and 30c in a distinguishable way by differentiating, through at least one of a type of line, darkness or shading of a line, a type of color and darkness of a color, the diagnosis information 30b and the diagnosis information 30c from each other. In one example, the lesions 30b and 30c, respectively, located on the front side and the rear side of the reference cross-section, are displayed with a dotted line to be distinguishable from the lesion 30a corresponding to the reference cross-section 20. In addition, in order to distinguish the lesions 30b and 30c from each other, the lesion 30b located on the front side of the reference cross-section 20 is displayed with a blurred line, whereas the lesion 30c located on the rear side of the reference cross-section 20 is displayed with a darker line.

In accordance with an illustrative example, when displaying lesions or bookmarks within the reference cross-section 20, the information display unit 220 displays detailed information 31b and 31c regarding the lesions or the bookmarks at a predetermined location on a screen. Alternatively, under the control of the input processing unit 220, in response to a user selecting a lesion or bookmark, the information display unit 220 displays detailed information regarding the selected lesion or bookmark on the screen. In accord with an example, the detailed information to be displayed on the screen includes shape, texture, and boundary of the lesion, a result of the diagnosis of the lesion, distance information between a cross-section that contains the lesion or bookmark, the reference cross-section, and a relative location, for example, a front side, a rear side, a left side and/or a right side, of the different cross-section in relation to the reference cross-section.

In the above embodiments, a user is able to receive diagnosis information corresponding to a different cross-section displayed in the cross-section or the diagnosis information located on the front side, the rear side, the left side, and/or the right side of the reference cross-section. In addition, the user is visually able to determine a relative location of each lesion in relation to the reference cross-section. Even in the case where there is no diagnosis information of a detected lesion or bookmark corresponding to the reference cross-section 20, diagnosis information corresponding to a different cross-section may be displayed within the reference cross-section 20. In this way, a user is able to recognize a relative location of the diagnosis information in relation to the reference cross-section 20 when the reference cross-section 20 is displayed, thereby preventing an omission of diagnosing a lesion.

In one illustrative configuration, all lesions or diagnosis information corresponding to different cross-sections, or some of all the lesions or diagnosis information corresponding to different cross-sections may be displayed within the reference cross-section. For example, it is possible to display only lesions or diagnosis information located on the front side, the rear side, the left side, and/or the right side of the reference cross-section that are closest to the reference cross-section. In the alternative, it is possible to display only lesions or diagnosis information located on two or three front sides, two or three rear sides, two or three left sides, and/or two or three right sides of the reference cross-section. In addition, although not located to be closest to the reference cross-section, some of lesions or diagnosis information corresponding to different cross-sections may be selectively displayed within the reference cross-section.

Figure 3A:
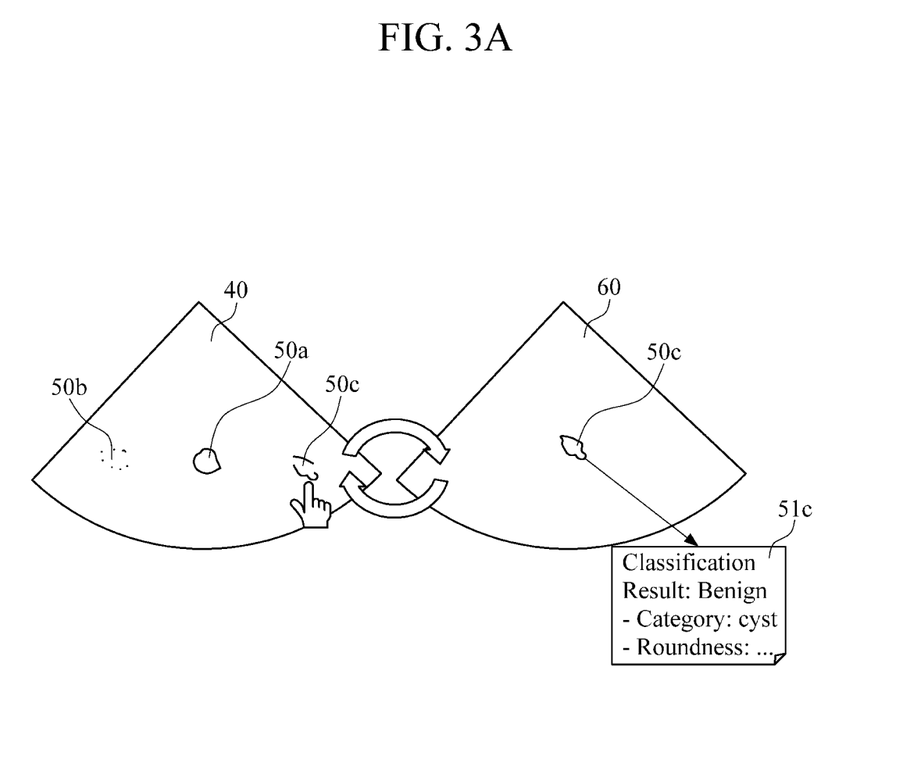
FIGS. 3A and 3B are diagrams illustrating an example in which a user input is processed.
Figure 3B:
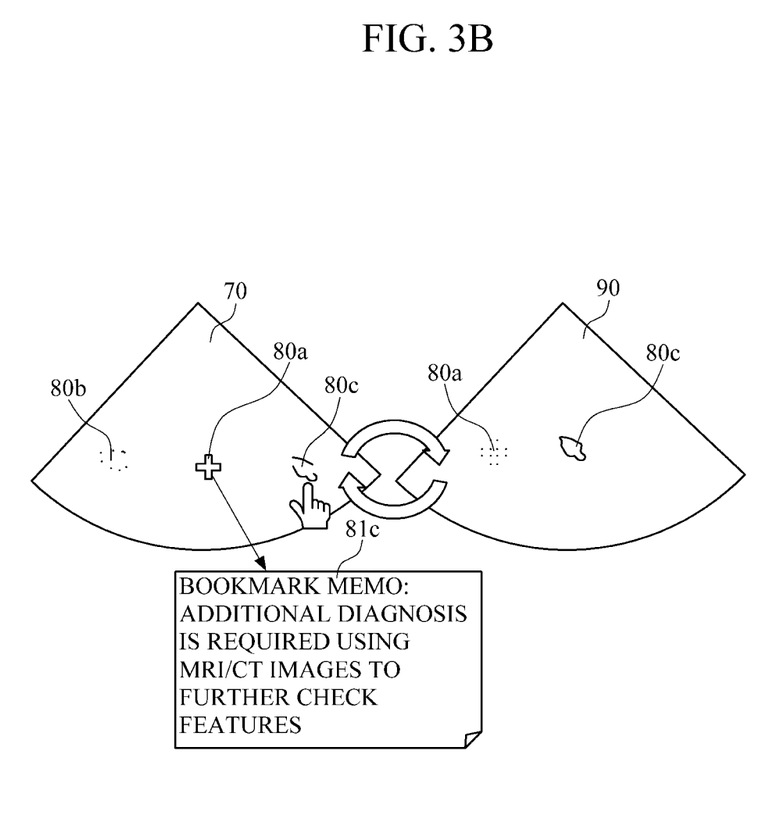

FIGS. 3A and 3B are diagrams illustrating an example of processing a user input, in accordance with an illustrative example.

The left-handed side of FIG. 3A shows lesions 50a, 50b and 50c corresponding to different cross-sections of the 3D image, respectively, which the information display unit 220 displays within the reference cross-section. A user is able to select a lesion using an input device, such as a mouse, a finger or a touch pen, to make desired detailed information shown. The input processing unit 230 receives the user's selection and performs an operation corresponding to the user's selection. The right-handed side of FIG. 3A shows a processing result of the input processing unit 230 when a user selects the lesion 50c located on a front side of the reference cross-section 40 from among the lesions 50a, 50b and 50c shown in the left-handed side of FIG. 3A.

In one example, in response to the user selecting the lesion 50c located on the front side of the reference cross-section 40, the input processing unit 230 controls the image display unit 210 to display the cross-section 60 containing the lesion 50c on a screen. In addition, when the cross-section 60 is displayed on the screen, the input processing unit 230 controls the information display unit 220 to display the lesion 50c within the cross-section 60. In one configuration, although not illustrated in FIG. 3B, the lesions 50a and 50b may also be displayed within the cross-section 60, if the user so desires. In addition, the input processing unit 230 controls the information display unit 220 to display detailed information 51c at a specific location on the screen. In one example, the information display unit 220 displays the detailed information 51c at a predetermined location on the screen at all times or in the case when a user moves an input device, such as a mouse, into a location of the lesion 50c or clicks on the right button of the mouse on a location of the lesion 50c.

FIG. 3B is a diagram for explaining an example to process a request from a user to generate a bookmark, in accordance with an illustrative example.

In the middle of examining a reference cross-section 70, in addition to the lesions that the lesion analyzing unit 120 detected, the diagnosis apparatus 100 and the diagnosis aiding apparatus 200 enable a user to explore other areas of the organ or tissue. In addition, a user may wish to run further tests or diagnostics on a lesion detected by the lesion analyzing unit 120 using Magnetic Resonance Imaging (MRI) or Computed Tomography (CT). In such case, a user may request to generate a bookmark to mark other areas of the organ or tissue that may be desired to be further analyzed or explored. In such case, as shown in FIG. 3B, the input processing unit 230 receives the user's request for bookmark generation and generates a bookmark 80a at a requested location in the reference cross-section 70. In addition, in response to a user inputting memo information 81c about the bookmark 80a, the input processing unit 230 receives the memo information 81c and stores a bookmark generation location and the memo information 81c as diagnosis information.

As such, the information display unit 220 displays the generated bookmark within the reference cross-section 70 on the screen. If a user selects diagnosis information regarding a lesion, for example, a lesion 80c located on the front side of the cross-section 70 in which the bookmark 80a is displayed, the information display unit 220 displays a cross-section 90 containing the lesion 80c under the control of the input processing unit 230. The information display unit 220 also displays the bookmark 80a corresponding to a rear side of the cross-section 90 in a distinguishable way by differentiating a type of color, darkness of a color, a type of line, and darkness of a line for one of the lesion 80c and the bookmark 80a from that of the other. Although not illustrated in FIG. 3B, a lesion 80b corresponding to a rear side of the reference cross-section 90 may be displayed as well. In this case, the lesion 80b belongs to a further rear side of the reference cross-section 90 than the bookmark 80a. As a result, a more blurred line or a less dark color is used for the lesion 80b than for the bookmark 80a to then show a relative location of the lesion 80b in relation to the lesion 80c of the reference cross-section 90.

Figure 4:
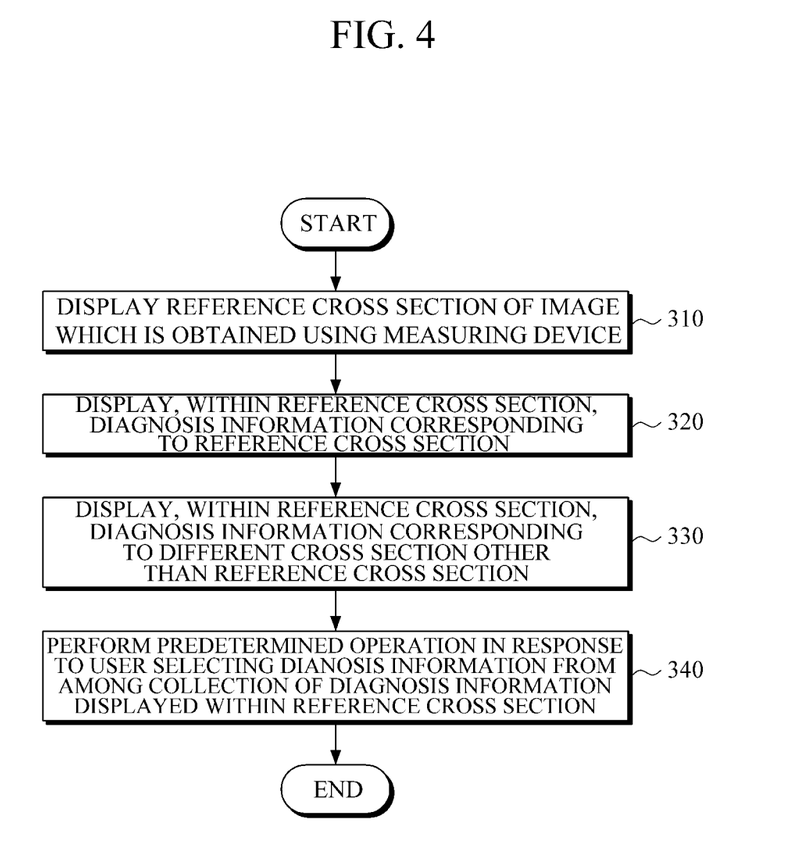
FIG. 4 is a flow chart illustrating a diagnosis aiding method, according to an illustrative example.

FIG. 4 is a flow chart illustrating a diagnosis aiding method, according to an illustrative example.

With reference to FIG. 4, the diagnosis aiding method using the diagnosis aiding apparatus 200 illustrated in FIG. 1 will be described.

At operation 310, the method displays on a screen the reference cross-section of an image obtained from a measuring device. At operation 320, the method displays diagnosis information, which corresponds to the reference cross-section, within the reference cross-section. In one example, the diagnosis information may include lesion diagnosis information and bookmark information. Furthermore, the lesion diagnosis information may include a lesion detected from the reference cross-section, shape, texture, and boundary of the lesion and a result of a diagnosis of the lesion. In turn, the bookmark information may be input by a user as a suspected area or an area required to be further diagnosed.

At operation 330, the method displays on the screen diagnosis information corresponding to a different or another cross-section within the reference cross-section on the screen. The method displays diagnosis information corresponding to the reference cross-section and diagnosis information corresponding to the different cross-section differently to enable the user to differentiate between the reference cross-section and the different cross-section make a diagnosis more accurately. In one example, the method displays the diagnosis information from the reference cross-section and the diagnosis information from the different cross-section in a distinguishable manner based on distance information, allowing the user to easily recognize a relative location of each lesion. As described above, the diagnosis information of the reference cross-section and the diagnosis information of the different cross-section may be displayed differently based on the distance information, a type of line, type of colors, darkness of a color or darkness of a line.

Furthermore, at operation 340, in response to the user operating a user interface (UI) through various input devices, such as a mouse, a finger or a touch pen, when the reference cross-section is displayed in a MPR view or full view of the screen, the method receives a user input corresponding to the UI operation and performs a predetermined operation corresponding to the user input. In one illustrative example, the predetermined operation is an operation to display detailed information of the selected diagnosis information at a predetermined location on the screen in which the reference cross-section is displayed, or an operation to display the different cross-section containing the selected diagnosis information and then displaying the selected diagnosis information within the different cross-section.

Furthermore, the method displays on the screen the different cross-section for a predetermined length of time, and displays the reference cross-section again after the predetermined length of time. Accordingly, a user is able to check the different cross-section and the reference cross-section in a continuous manner without moving the ultrasound measuring device, such as a probe.

Figure 5:
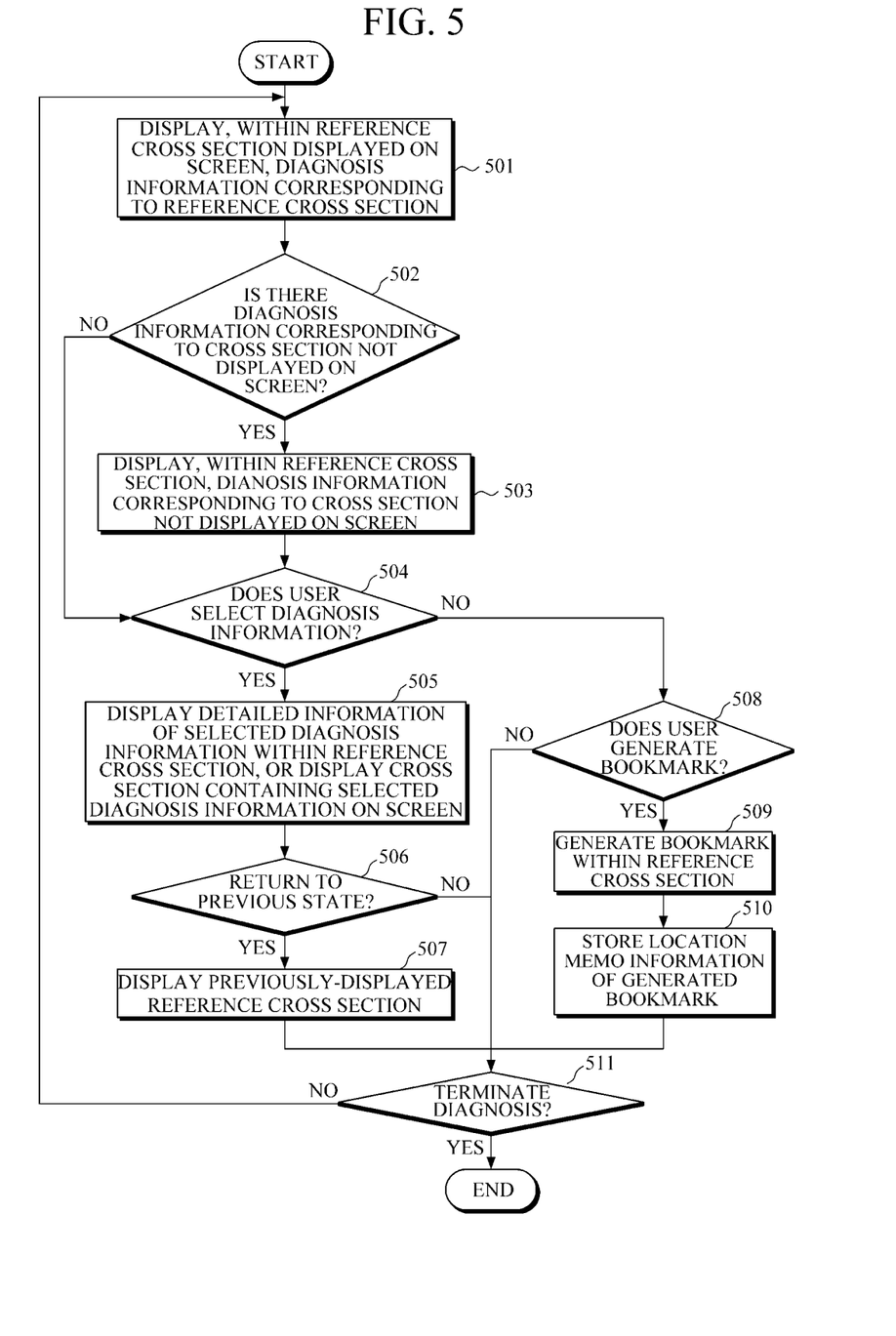
FIG. 5 is a flow chart illustrating the diagnosis aiding method, according to an illustrative example.

FIG. 5 is a flow chart illustrating a diagnosis aiding method performed at the diagnosis aiding apparatus 200, according to an illustrative example.

At operation 501, the method displays the reference cross-section measured by the ultrasound measuring device in MPR view or full view on a screen. When there is diagnosis information corresponding to the reference cross-section, the method also displays the diagnosis information within the reference cross-section. The displayed diagnosis information may include lesion diagnosis information generated by the diagnosis apparatus 100 and bookmark information generated by a user input.

At operation 502, the method determines whether there is diagnosis information corresponding to a different cross-section other than the reference cross-section. In other words, the method determines whether there is diagnosis information corresponding to a different cross-section that is not displayed on the screen. At operation 503, the diagnosis aiding apparatus 200 displays the diagnosis information corresponding to the different cross-section within the reference cross-section. As described above with reference to FIGS. 2A and 2B, the method of the diagnosis aiding apparatus 200 displays the diagnosis information corresponding to the different cross-section within the reference cross-section differently to be distinguished from the diagnosis information corresponding to the reference cross-section by differentiating type of colors, a type of line, darkness of a color or darkness of a line.

Alternatively, the method displays diagnosis information located on the front, the rear side, the left side, or the right side of the reference cross-section in a distinguishable manner to provide the user with information indicating whether the diagnosis information is located on the front side, the rear side, the left side, or the right side of the reference cross-section. In addition, the method may provide distance information between the different cross-section containing the diagnosis information and the reference cross-section, and display the diagnosis information by differentiating, based on the distance information, a type of line, type of colors, darkness of a line or darkness of a color, between the diagnosis information corresponding to the different cross-section and the diagnosis information of the reference cross-section. In this manner, the method enables the user to easily recognize a relative location of the diagnosis information in relation to the reference cross-section.

At operation 504, in response to a user input received through a UI manipulation when the reference cross-section is displayed on the screen, the method determines whether the user input corresponding to the UI manipulation is selecting specific diagnosis information from among a collection of diagnosis information displayed on the screen.

If the user input selects specific diagnosis information, at operation 505, the method displays detailed information of the selected diagnosis information within the reference cross-section or displays a cross-section containing the selected diagnosis information on the screen. In one illustrative example, the method displays the selected diagnosis information and the detailed information of the selected diagnosis information in the different cross-section. At operation 506, the method determines whether to return to a previous state. If a predetermined length of time lapses or if the user requests to return to the previous state, at operation 507, the method displays the previously-displayed reference cross-section. Otherwise, if the method determines not to return to a previous state, the method moves to operation 511 to determine whether to terminate diagnosis.

Back to operation 504, if the method determines that the user input is not the selection of the specific diagnosis information, at operation 508, the method determines whether the user input is a request for bookmark generation. If the method determines that the user input is a request for bookmark generation, at operation 509, the method generates a bookmark on a location requested by the user. At operation 510, the method stores a location of the generated bookmark and memo information the user input. If at operation 508 the method determines that the user input is not a request for bookmark generation, the method proceeds to operation 511 to determine whether to terminate diagnosis.

At operation 511, the method determines whether a diagnosis is terminated. If it is determined that the diagnosis is terminated, the diagnosis is terminated or ends. Alternatively, the method returns to operation 501 and prepares to receive an image and, in response to the image being received, the method displays the received image again.

Program instructions to perform the methods of FIGS. 4 and 5, or one or more operations thereof, may be recorded, stored, or fixed in one or more non-transitory computer-readable storage media. The program instructions may be implemented by a computer. For example, the computer may cause a processor to execute the program instructions. The media may include, alone or in combination with the program instructions, data files, data structures, and the like.

Examples of computer-readable media include magnetic media, such as hard disks, floppy disks, and magnetic tape; optical media such as CD ROM disks and DVDs; magneto-optical media, such as optical disks; and hardware devices that are specially configured to store and perform program instructions, such as read-only memory (ROM), random access memory (RAM), flash memory, and the like. Examples of program instructions include machine code, such as produced by a compiler, and files containing higher level code that may be executed by the computer using an interpreter. The program instructions, that is, software, may be distributed over network coupled computer systems so that the software is stored and executed in a distributed fashion. For example, the software and data may be stored by one or more computer readable recording mediums. Also, functional programs, codes, and code segments for accomplishing the example embodiments disclosed herein can be easily construed by programmers skilled in the art to which the embodiments pertain based on and using the flow diagrams and block diagrams of the figures and their corresponding descriptions as provided herein.

A number of examples have been described above. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A diagnosis aiding apparatus, comprising:
a memory, configured to store instructions; and
one or more processors, that upon executing the stored instructions, are configured to:
  display one (hereinafter, a reference cross-section) among a plurality of cross-sections forming a three-dimensional (3D) volume image on a screen,
  display at least one first diagnosis information corresponding to at least one first lesion existing in the reference cross-section within the reference cross-section currently displaying on the screen by detecting and analyzing the at least one first lesion existing in the reference cross-section,
  determine whether there is at least one second diagnosis information corresponding to at least one second lesion existing in at least one different cross-section among the plurality of cross-sections by detecting and analyzing the at least one second lesion existing in the at least one different cross-section, the at least one different cross-section being currently not displayed on the screen, and
  in response to a result of the determination being that there is the at least one second diagnosis information, display the at least one second diagnosis information within the reference cross-section currently displaying on the screen such that the at least one first diagnosis information and the at least one second diagnosis information are concurrently displayed on the reference cross-section,
wherein the at least one first diagnosis information comprises a shape of the first lesion, and
wherein the at least one second diagnosis information comprises a boundary line of the second lesion corresponding to distance information between the reference cross-section and the different cross-section comprising the second lesion, and bookmark information.

2. The diagnosis aiding apparatus as recited in claim 1, wherein, the one or more processors are further configured to:

display the at least one second diagnosis information differently based on distance information between the reference cross-section and each of the at least one different cross-sections.

3. The diagnosis aiding apparatus as recited in claim 2, wherein the one or more processors are further configured to:

display the at least one second diagnosis information differently based on at least one of a type of color, darkness of a color, a type of line or darkness of a line for the at least one second diagnosis information of each of the at least one different cross-sections from that of the at least one first diagnosis information of the reference cross-section.

4. The diagnosis aiding apparatus as recited in claim 1, wherein, in response to diagnosis information located on each of a front side and a rear side of the reference cross-section, the one or more processors are further configured to:

display the diagnosis information located on each of the front side and the rear side differently based on at least one of a type of color, darkness of a color, a type of line or darkness of a line for the diagnosis information located on one of the front side and the rear side from that of the diagnosis information located on the other side.

5. The diagnosis aiding apparatus as recited in claim 1, wherein the one or more processors are further configured to:

perform an operation in accordance with diagnosis information selected by a user from among a collection of diagnosis information displayed within the reference cross-section.

6. The diagnosis aiding apparatus as recited in claim 5, wherein, in response to diagnosis information corresponding to one of the at least one different cross-section from the reference cross-section, being selected, the one or more processors are further configured to control a different cross-section corresponding to the selected diagnosis information to be displayed.

7. The diagnosis aiding apparatus as recited in claim 6, wherein the one or more processors are further configured to:

control the different cross-section corresponding to the selected second diagnosis information to be displayed for a length of time, and control the reference cross-section to be displayed on the screen again after the length of time.

8. The diagnosis aiding apparatus as recited in claim 6, wherein, in response to the displaying of the different cross-section corresponding to the selected second diagnosis information, the one or more processors are further configured to:

display, within the different cross-section displayed on the screen, both the diagnosis information corresponding to the different cross-section corresponding to the selected second diagnosis information and the first diagnosis information corresponding to the reference cross-section that disappears on the screen due to the displaying of the different cross-section corresponding to the selected second diagnosis information.

9. The diagnosis aiding apparatus as recited in claim 1, wherein the one or more processors are further configured to:

display, in an overlapping manner, detailed information of diagnosis information, that is selected from among the at least one first diagnosis information, with different diagnosis information at a predetermined location within the reference cross-section.

10. The diagnosis aiding apparatus as recited in claim 5, wherein the one or more processors are further configured to:

generate a bookmark on the displayed reference cross-section, and store bookmark information containing a location of the bookmark and additional memo information input by the user.

11. A diagnosis aiding method, comprising: displaying one (hereinafter, a reference cross-section) among a plurality of cross-sections forming a three-dimensional (3D) volume image on a screen;

displaying at least one first diagnosis information corresponding to at least one first lesion existing in the reference cross-section within the reference cross-section currently displaying on the screen by detecting and analyzing the at least one first lesion existing in the reference cross-section;

determining whether there is at least one second diagnosis information corresponding to at least one second lesion existing in at least one different cross-section among the plurality of cross-sections by detecting and analyzing the at least one second lesion existing in the reference cross-section, the at least one different cross-section being currently not displayed on the screen; and in response to a result of the determining being that there is the at least one second diagnosis information, displaying the at least one second different diagnosis information within the reference cross-section currently displaying on the screen such that the at least one first diagnosis information and the at least one second diagnosis information are concurrently displayed on the reference cross-section, wherein the at least one first diagnosis information comprises a shape of the first lesion, and wherein the at least one second diagnosis information comprises a boundary line of the second lesion corresponding to distance information between the reference cross-section and the different cross-section comprising the second lesion, and bookmark information.

12. The diagnosis aiding method as recited in claim 11, wherein the displaying of the at least one second diagnosis information comprises:

displaying the at least one second diagnosis information differently based on the distance information.

13. The diagnosis aiding method as recited in claim 12, wherein the displaying of the at least one second diagnosis information differently comprises:

displaying the at least one second diagnosis information differently based on at least one of a type of color, darkness of a color, a type of line or darkness of a line for the at least one second diagnosis information corresponding to the at least one different cross-section from that of the at least one first diagnosis information corresponding to the reference cross-section.

14. The diagnosis aiding method as recited in claim 11, wherein the displaying of the at least one second diagnosis information comprises:

in response to diagnosis information located on each of a front side and a rear side of the reference cross-section, displaying the diagnosis information located on one of the front side and the rear side differently based on at least one of a type of color, darkness of a color, a type of line or darkness of a line between the diagnosis information located on one of the front side and the rear side from that of the diagnosis information located on the other side.

15. The diagnosis aiding method as recited in claim 11, further comprising:
in response to a selection of one from among the at least one first diagnosis information and the at least one second diagnosis information displayed within the reference cross-section on the screen, performing an operation in accordance with the selection.

16. The diagnosis aiding method as recited in claim 15, wherein the performing of the operation comprises:
in response to a selection of one of the at least one second diagnosis information, controlling a different cross-section corresponding to the selected second diagnosis information to be displayed on the screen.

17. The diagnosis aiding method as recited in claim 16, wherein the performing of the operation comprises:
controlling the different cross-section corresponding to the selected diagnosis information on the screen for a length of time, and
controlling the reference cross-section to be displayed on the screen again after the length of time.

18. The diagnosis aiding method as recited in claim 15, wherein the performing of the operation comprises:
in response to a selection of one of the at least one first diagnosis information, controlling a detailed information of the selected first diagnosis information to be displayed on a predetermined location within the reference cross-section in an overlapping manner.

19. The diagnosis aiding method as recited in claim 11, further comprising:
generating a bookmark within the reference cross-section on the screen; and
storing bookmark information containing a location of the bookmark and additional memo information of the bookmark.

20. A diagnosis system, comprising:
a diagnosis apparatus configured to:
detect at least one first lesion from a plurality of cross-sections forming a three-dimensional (3D) volume image,
analyze the at least one first lesion, and
generate diagnosis information corresponding to the plurality of cross-sections regarding the at least one first lesion; and
a diagnosis aiding apparatus configured to:
display one (hereinafter, reference cross-section) among the plurality of cross-sections on a screen,
display, within the reference cross-section currently displaying on the screen, at least one first diagnosis information corresponding to at least one first lesion existing in the reference cross-section by detecting and analyzing the at least one first lesion existing in the reference cross-section,
determine whether there is at least one second diagnosis information corresponding to at least one second lesion existing in at least one different cross-section among the plurality of cross-sections by detecting and analyzing the at least one second lesion existing in the at least one different cross-section, the at least one different cross-section being currently not displayed on the screen, and
in response to a result of the determining being that there is the at least one second diagnosis information, display the at least one second diagnosis information within the reference cross-section currently displaying on the screen such that the at least one first diagnosis information and the at least one second diagnosis information are concurrently displayed on the reference cross-section,
wherein the at least one first diagnosis information comprises a shape of the first lesion, and
wherein the at least one second diagnosis information comprises a boundary line of the second lesion corresponding to distance information between the reference cross-section and the different cross-section comprising the second lesion, and bookmark information.

21. The diagnosis system as recited in claim 20, wherein the diagnosis aiding apparatus is further configured to:
display the at least one first diagnosis information and the at least one second diagnosis information differently based on distance information between the reference cross-section and each of the at least one different cross-section.

22. The diagnosis system as recited in claim 20, wherein the diagnosis aiding apparatus is further configured to display, in response to a selection of one of the at least one second diagnosis information, the different cross-section corresponding to the selected second diagnosis information on the screen.

23. The diagnosis system as recited in claim 22, wherein, when displaying the different cross-section corresponding to the selected second diagnosis information on the screen, the diagnosis aiding apparatus is further configured to:
display, within the different cross-section corresponding to the selected second diagnosis information, diagnosis information corresponding to the different cross-section corresponding to the selected second diagnosis information and the first diagnosis information of the reference cross-section, which disappears on the screen due to the displaying of the different cross-section corresponding to the selected second diagnosis information.

24. A diagnosis aiding apparatus, comprising:
a memory, configured to store instructions; and
an information display processor, that upon executing the stored instructions, is configured to:
display, within one (hereinafter, a reference cross-section) currently displaying among a plurality of cross-sections forming a three-dimensional (3D) volume image, at least one first diagnosis information corresponding to at least one first lesion existing in the reference cross-section by detecting and analyzing the at least one first lesion existing in the reference cross-section,
determine whether there is at least one second diagnosis information corresponding to at least one second lesion existing in at least one different cross-section among the plurality of cross-sections by detecting and analyzing the at least one second lesion existing in the at least one different cross-section, the at least one different cross-section being currently not displayed on the screen,
in response to a result of the determining being that there is the at least one second diagnosis information, display the at least one second diagnosis information within the reference cross-section currently displaying on the screen such that the at least one first diagnosis information and the at least one second diagnosis information are concurrently displayed on the reference cross-section, and display distance information between the reference cross-section and the at least one different cross-section as diagnosis information of an area of interest in the image,
wherein the at least one first diagnosis information comprises a shape of the first lesion, and
wherein the at least one second diagnosis information comprises a boundary line of the second lesion corresponding to distance information between the reference cross-section and the different cross-section comprising the second lesion, and bookmark information.

25. The diagnosis aiding apparatus as recited in claim 24, wherein the at least one first diagnosis information and the at least one second diagnosis information further comprises lesion diagnosis information and bookmark information.

26. The diagnosis apparatus as recited in claim 24, wherein the information display processor is further configured to:
display the at least one first diagnosis information and the at least one second diagnosis information differently based on distance information between the reference cross-section and each of the at least one different cross-section.

27. The diagnosis aiding apparatus as recited in claim 26, wherein the information display processor is further configured to:
display the at least one first diagnosis information and the at least one second diagnosis information differently based on at least one of a type of line, type of colors, darkness of a color, or darkness of a line.

28. The diagnosis aiding apparatus as recited in claim 24, wherein the information display processor is further configured to:
display in response to a selection of one of the at least one second diagnosis information, the different cross-section corresponding to the selected second diagnosis information for a length of time, and
display the reference cross-section again after the length of time.

29. The diagnosis aiding apparatus as recited in claim 24, wherein the information display processor is further configured to:
display bookmark information input from a user as a suspected area or an area required to be further diagnosed.

30. The diagnosis aiding apparatus as recited in claim 24, wherein the information display processor is further configured to:
display within the reference cross-section, the at least one first diagnosis information of the reference cross-section and at least one second diagnosis information of different cross-sections located on a front side and a rear side, or on a left side and a right side of the reference cross-section.

31. The diagnosis aiding apparatus as recited in claim 25, wherein the lesion diagnosis information further comprises shape, texture, and a boundary line of the lesion.

32. The diagnosis aiding apparatus as recited in claim 24, further comprising:
an input processing processor configured to generate a bookmark at a location in the reference cross-section and receive memo information about the bookmark.

33. An apparatus, comprising:
an image displaying processor configured to display one (hereinafter, a reference cross-section) among a plurality of cross-sections forming a three-dimensional (3D) volume image on a screen; and
an information display processor configured to:
display at least one first diagnosis information corresponding to at least one first lesion at a location in the reference cross-section within the reference cross-section currently displaying by detecting and analyzing the at least one first lesion existing in the reference cross-section,
determine whether there is at least one second diagnosis information of at least one second lesion corresponding to at least one different cross-section among the plurality of cross-sections by detecting and analyzing the at least one second lesion existing in the at least one different cross-section, the at least one different cross-section being currently not displayed on the screen, and
in response to a result of the determining being that there is the at least one second diagnosis information, display the at least one second diagnosis information at other locations in the reference cross-section providing a relative location of each lesion in relation to the reference cross-section such that the at least one first diagnosis information and the at least one second diagnosis information are concurrently displayed on the reference cross-section,
wherein the at least one first diagnosis information comprises a shape of the first lesion, and
wherein the at least one second diagnosis information comprises a boundary line of the second lesion corresponding to distance information between the reference cross-section and the different cross-section comprising the second lesion, and bookmark information.

34. The apparatus as recited in claim 33, wherein the information display processor is further configured to display bookmarks at a predetermined location on the screen.

35. The apparatus as recited in claim 33, wherein the information display processor is further configured to:
display all lesions or diagnosis information corresponding to the at least one different cross-section, or some of all the lesions or diagnosis information corresponding to the at least one second different cross-sections within the reference cross-section.

36. The apparatus as recited in claim 33, further comprising:
an image obtaining processor configured to generate the 3D volume image data using cross-sections of an area of interest in a patient; and
a lesion analyzing processor configured to calculate distance information between the reference cross-section and the at least one different cross-section to generate diagnosis information of the area of interest.

37. The apparatus as recited in claim 33, further comprising:
an input processing processor configured to generate a bookmark at a location in the reference cross-section and receive memo information about the bookmark.

38. The diagnosis aiding apparatus as recited in claim 1, wherein the one or more processors comprise:
an image display processor configured to display the reference cross section of the image on the screen;
an information display processor configured to:
display the at least one first diagnosis information on the screen, and
display the at least one second diagnosis information within the reference cross-section displayed on the screen; and an input processing processor configured to select one of diagnosis information within the reference cross-section.

* * * * *